US00PP36412P2

(12) United States Plant Patent
Thompson et al.

(10) Patent No.: US PP36,412 P2
(45) Date of Patent: Jan. 28, 2025

(54) BLACKBERRY PLANT NAMED 'HFG B2008T'

(50) Latin Name: ***Rubus* L. *subgenus Rubus***
Varietal Denomination: HFG B2008T

(71) Applicants: Ellen Thompson, Watsonville, CA (US); Max Laddon, Santa Cruz, CA (US)

(72) Inventors: Ellen Thompson, Watsonville, CA (US); Max Laddon, Santa Cruz, CA (US)

(73) Assignee: Hortifrut Genetics Limited, Dublin (IE)

( * ) Notice: Subject to any disclaimer, the term of this patent is extended or adjusted under 35 U.S.C. 154(b) by 0 days.

(21) Appl. No.: 18/638,468

(22) Filed: Apr. 17, 2024

(51) Int. Cl.
*A01H 5/08* (2018.01)
*A01H 6/74* (2018.01)

(52) U.S. Cl.
USPC ..... Plt./203
CPC ..... *A01H 6/7499* (2018.05)

(58) Field of Classification Search
USPC ..... Plt./203
CPC ..... A01H 6/7499; A01H 5/08
See application file for complete search history.

*Primary Examiner* — Keith O. Robinson
(74) *Attorney, Agent, or Firm* — King IP Law; Joshua King

(57) ABSTRACT

A new and distinct cultivar of blackberry named 'HFG B2008T' is characterized by its ability to be equally productive in both floricane and primocane cycles. It is characterized by mid-to late season production of consistently shaped, large fruit borne on erect spineless primocanes. This new cultivar is identified, among other things, by its high vigor, extreme firmness, and ability to maintain a low rate of color reversion even under rainy conditions and/or moderate pressure of spotted wing drosophila (*Drosophila suzukii* Matsumura).

4 Drawing Sheets

Latin name of the genus and species of the plant claimed: *Rubus* L. subgenus *Rubus*.

Variety denomination: 'HFG B2008T'.

BACKGROUND OF THE INVENTION

Blackberries are a commercially important member of the Rosaceae (rose) family, Rosoideae subfamily, known botanically as *Rubus* L. subgenus *Rubus* Watson. Rosaceae is considered the sixth most economically important crop family which includes apple, almond, cherry, peach, plum, raspberry and strawberry, among many others.

Plants in the *Rubus* genus are unique in that they have perennial root systems from which biennial canes are borne. Like raspberries (*Rubus idaeus*), blackberry fruits are formed by an aggregation of individual drupelets attached to a fleshy torus (receptacle). Unlike raspberries, the torus remains connected to the blackberry drupelets upon harvest and is consumed. Each drupelet contains a seed (pyrene), that is surrounded by a fleshy mesocarp (pulp) and exocarp (fruit skin). Blackberries are well-documented for their health benefits and a known source for secondary plant metabolites including anthocyanins, phenolics, tannins and flavonoids. Worldwide blackberries are wild-collected, cultivated, and consumed as jams, jellies, juice, frozen and fresh products.

Production of fresh-market blackberries has expanded significantly over the past 25 years, and fruits are now in demand globally. Advances in blackberry breeding, particularly the development of primocane-fruiting (remontancy) by the University of Arkansas, has enhanced the ability to produce crops in non-temperate regions where berries have not been grown historically. Additionally, selection pressure for firmness has allowed for blackberries to be shipped internationally to the high-demand markets in North America and across Europe.

Seeds of the present cultivar, 'HFG B2008T', were created from a controlled cross using hand-pollination. The cross was prepared in 2018 in Watsonville, Santa Cruz County, California between the proprietary maternal parent 'PBB 1616T' (U.S. Plant Pat. No. 33,721 P2) and proprietary paternal parent selection 'B1611T' (unpatented). Seeds from this controlled pollination were extracted, germinated and sowed in spring 2019. The following spring (2020), a plant within this seedling family with superior characteristics was identified and designated as selection 'HFG B2008T'. Test plots of 'HFG B2008T' were subsequently planted for evaluation and deemed to be unique, distinct, stable and desirable.

'HFG B2008T' offers significant advantages over the existing, patented primocane-fruiting blackberry variety 'APF-45' marketed under the tradename Prime-Ark® 45 (U.S. Plant Pat. No. 22,449). Another example of an existing, patented primocane-fruiting blackberry variety is 'APF-122' (U.S. Plant Pat. No. 28,598). A further example of an existing primocane-fruiting blackberry variety is 'APF-190T' marketed under the trade name Prime-Ark® Traveler (U.S. Plant Pat. No. 28,589 P3).

Compared to 'APF-45', which is spiny, the present cultivar 'HFG B2008T' is spineless. Further, the present cultivar produces a significantly more productive floricane crop than 'APF-45'. The present cultivar has a more balanced cropload between floricane and primocane harvests.

Compared with 'APF-122', berries of the present invention are larger in size and firmer. Under postharvest storage conditions, 'HFG B2008T' develops less color reversion (drupelet reddening) after 7 days in cold storage than 'APF-122'.

Compared to 'APF-190T', 'HFG B2008T' displays more intensive flowering and fruiting during the primocane cycle.

Thus, 'HFG B2008T' is a new and distinct primocane-fruiting blackberry cultivar that can be identified, among other things, by its spinelessness, firmness, nearly balanced crop load between floricane and primocane cycles, low postharvest color reversion and increased intensity of its primocane-fruiting habit.

BRIEF DESCRIPTION OF THE PHOTOGRAPHS

DETAILED DESCRIPTION

Figure 1:
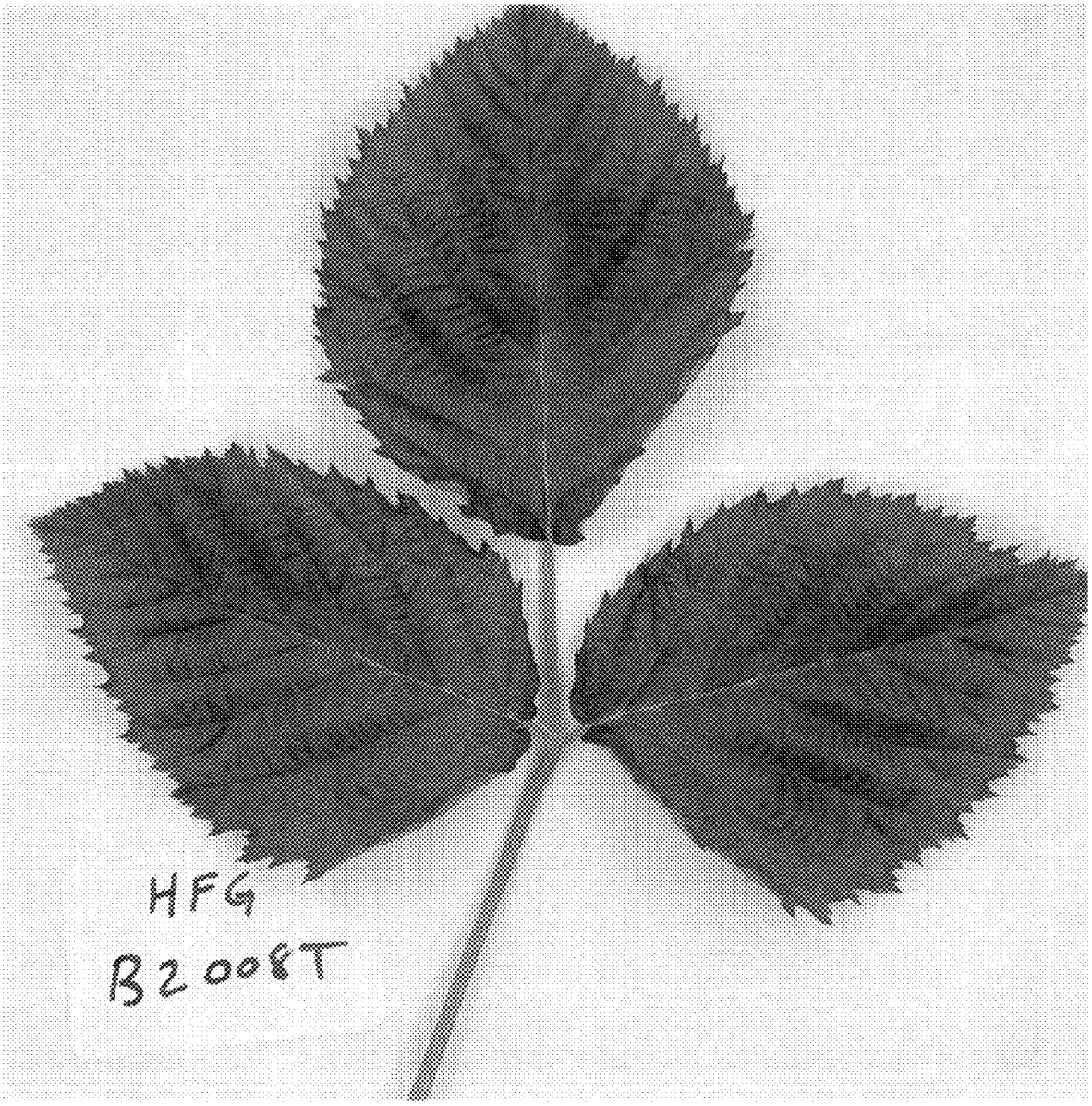
FIG. 1 is a photograph showing a typical trifoliate leaflet borne from reproductive buds of 'HFG B2008T'.
Figure 2:
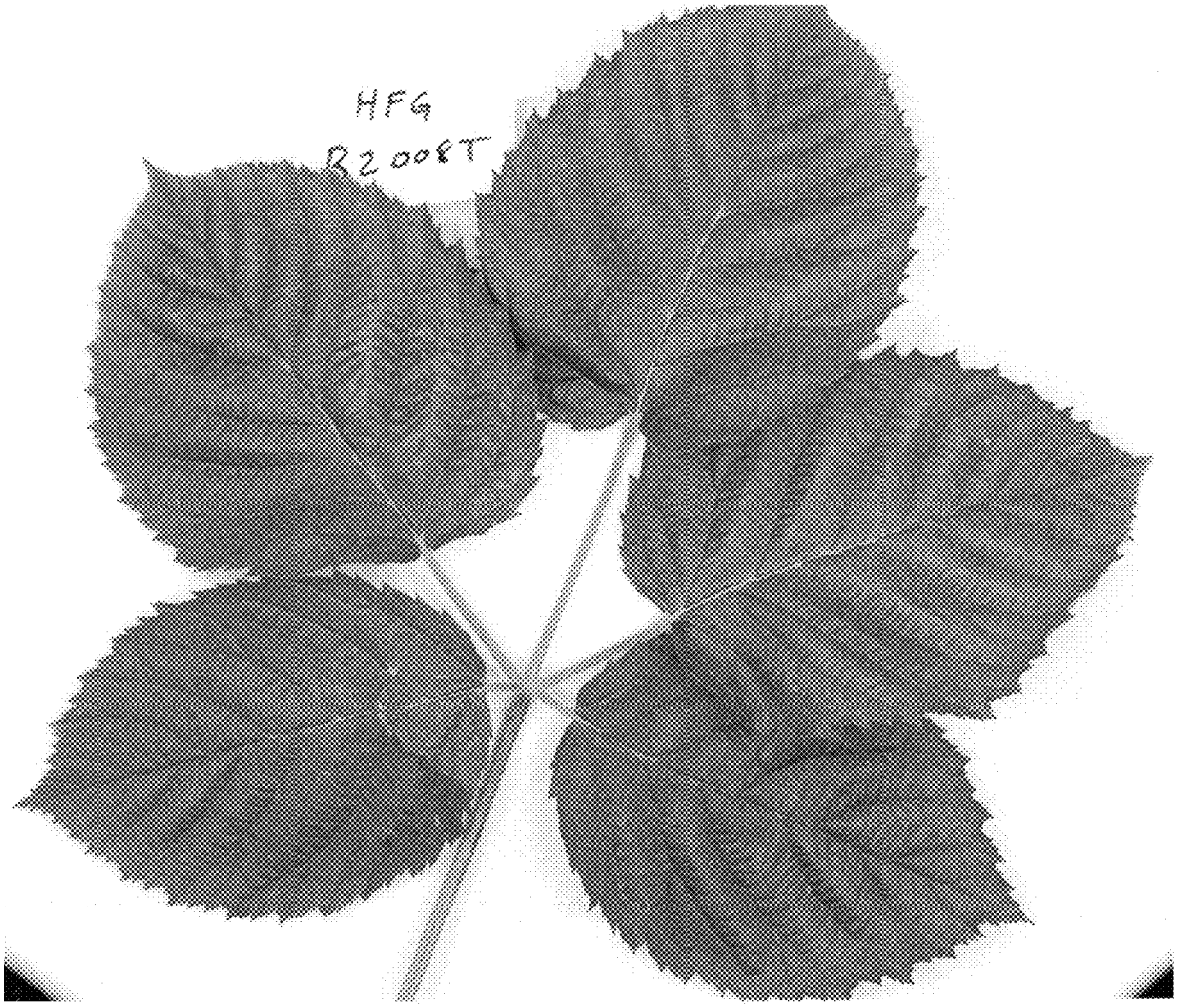
FIG. 2 is a photograph of a typical pentafoliate leaflet borne from vegetative buds of 'HFG B2008T'.
Figure 3:
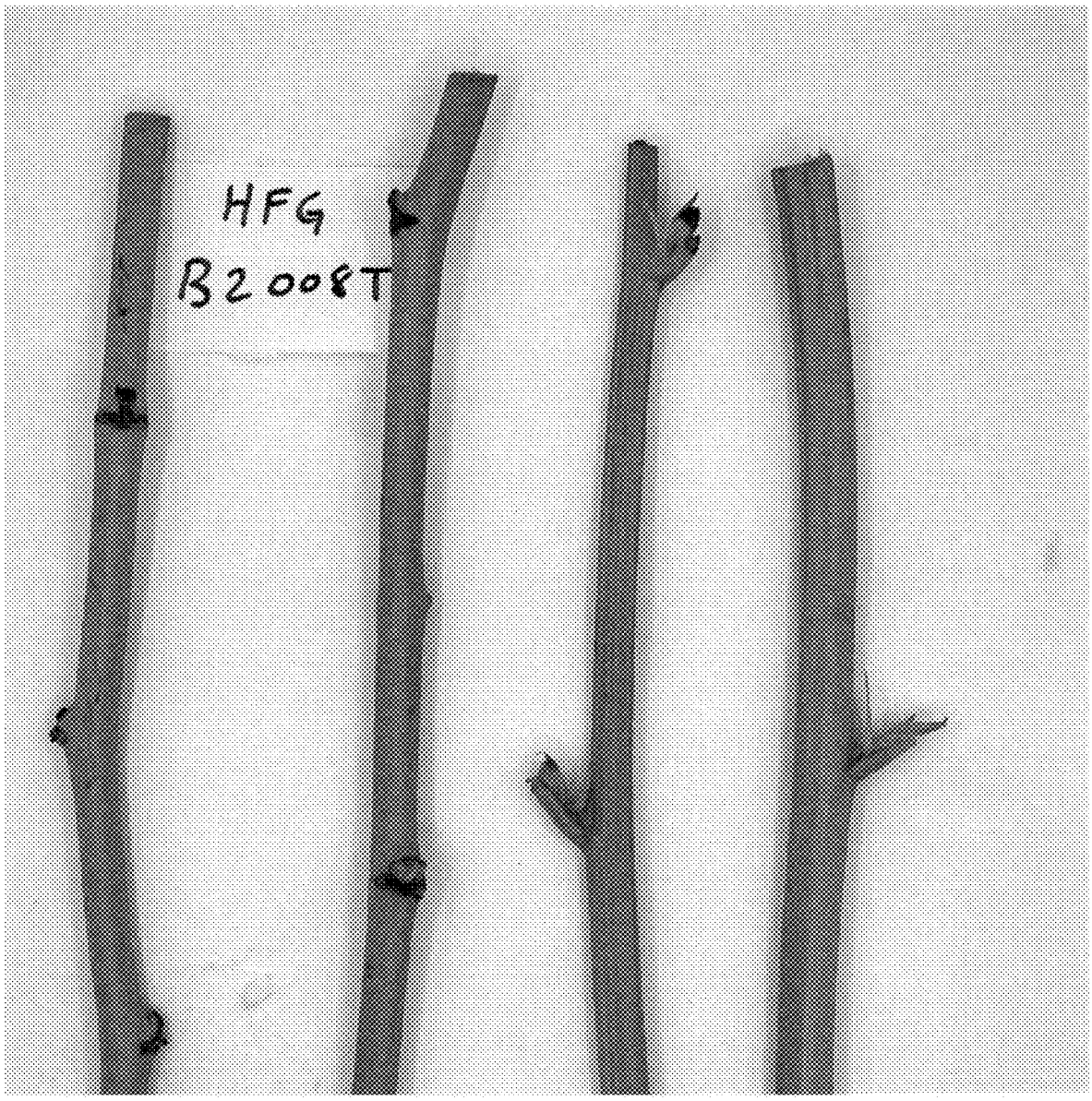
FIG. 3 is a photograph of a section of the spineless canes that are typical of 'HFG B2008T'.
Figure 4:
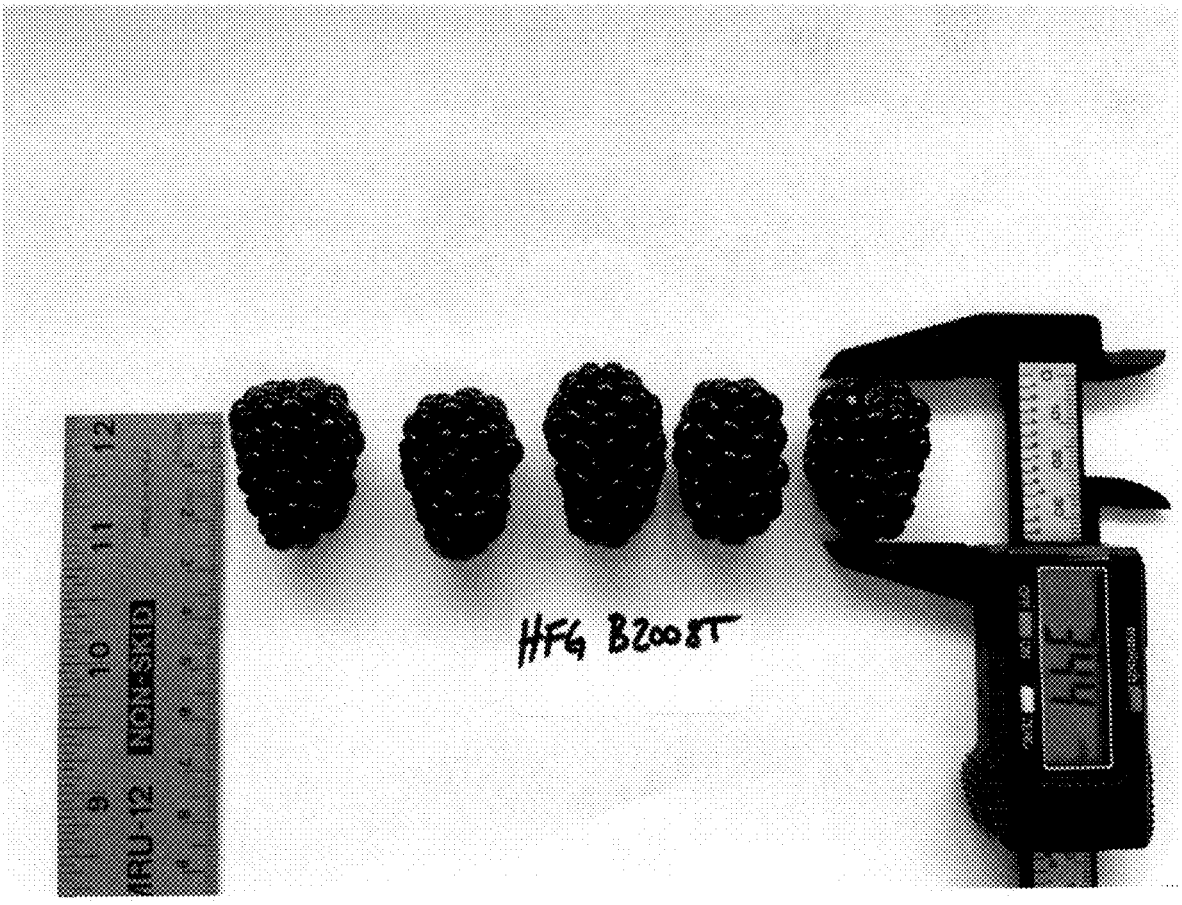
FIG. 4 is a photograph displaying the typical berry size, shape and dimensions of 'HFG B2008T'.

Note: statements of characteristics herein represent exemplary observations of the cultivar herein and will vary depending on time of year, location, annual weather, etc.

Cultivar name: 'HFG B2008T'.

Classification:

*Family*.—*Rosaceae*.

Botanical name: *Rubus* L. subgenus *Rubus* Watson.

*Common name*.—Blackberry.

Although blackberries (*Rubus* subgenus *Rubus* Watson) are highly heterogeneous and outcrossing and most clones contain genes from more than one species, the new cultivar and its progenitor lines phenotypically exhibit characters predominately of the erect eastern United States species, *Rubus allegheniensis* Porter (highbush blackberry).

Parentage:

*Female parent*.—'PBB 1616T' (U.S. Plant Pat. No. 33,721 P2).

*Male parent*.—'B1611T' (unpatented).

'HFG B2008T' was first identified in a substrate block with other seedlings in September 2020 in Santa Cruz County, California USA. 'HFG B2008T' was first propagated asexually by crown division in November 2020 at the same location of its discovery. The crown on the original plant was separated into basal cane pieces (approximately 15 cm long) with root attached and replanted into a single larger pot and placed inside a screenhouse on site. The remaining root pieces were chilled for 4 weeks, then planted inside a heated greenhouse to force adventitious shoots. Approximately 10 adventitious shoots were excised, rooted, and planted the following spring for further evaluation of the selection.

In September 2021, five young actively growing primocanes were virus tested, excised and shipped to McMinnville, Yamhill County, Oregon, USA, where the vegetative material was established in vitro for micropropagation. This tissue culture propagation method has allowed for additional, more extensive testing of 'HFG B2008T' and aided in determining that this cultivar is genetically stable.

Growing location for the observations herein: Watsonville, Santa Cruz County, California, USA.

Time of year (season): Spring and Autumn 2023.

Age of plants used for this discussion: 6 months for primocanes, 14 months for floricanes.

Age of plants used for the photographs in the figures: 6 months for primocanes, 14 months for floricanes.

Type of greenhouse covering or growing structure, or field: Substrate block with high tunnel over plants.

Light: Natural.

Pinch dates (if required): Not required.

Color terminology where noted were followed using The R.H.S. Colour Chart, Royal Horticultural Society, Fifth Edition, London, United Kingdom (2007).

Observations for floricanes herein were made in May 2023. Observations for primocanes herein were made in October 2023.

Plant:

*Form/shape*.—Vase, upright.

*Growth habit*.—Erect.

*Height*.—Floricanes — 111.8 cm and Primocanes — 241.3 as measured from cane base to cane apex.

*Spread*.—59.7 cm as measured from lateral leaf tip to lateral leaf tip.

*Propagation method*.—Tissue culture (in vitro).

*Time to initiate and develop roots*.—31 days.

*Root description*.—Fibrous.

*Young shoots*.—

*Anthocyanin coloration during rapid growth*.—Absent or very weak.

*Intensity of green coloration*.—Dark.

*Number of glandular hairs*.—Medium.

Primocanes:

*Cane Shape in cross-section*.—Rounded to angular.

*Diameter*.—*Base:* 1.0 cm | Middle: 0.9 cm | Tip: 0.7 cm.

*Length*.—219.2 cm.

*Number of nodes*.—32.

*Internode length*.—Base: 6.0 cm | Middle: 8.3 cm | Tip: 5.8 cm.

*Number of canes/pot*.—6.

*Cane color*.—Undertone is RHS 144A-RHS 144B; Overtone is RHS 183A.

*Spines* (*present or absent*).—Absent. Density: Base — N/A Middle — N/A Tip-N/A. Shape: N/A. Length: N/A. Width: N/A. Apex descriptor: N/A. Color: N/A.

*Bud shape*.—Elliptic. Length: 0.49 cm. Diameter (base): 0.11 cm. Diameter (tip): 0.07 cm. Color: RHS 144A. Texture: Mildly pubescent.

Floricanes:

*Cane shape in cross-section*.—Rounded to angular.

*Diameter*.—Base: 0.81 cm | Middle: 0.80 cm | Tip: 0.81 cm.

*Length*.—100.8 cm.

*Number of nodes*.—19.

*Internode length*.—Base: 5.9 cm | Middle: 6.4 cm | Tip: 6.3 cm.

*Cane color*.—Lower cane — RHS N144A. Upper cane — RHS N144A.

*Spines*.—Absent. Spine density: Base — N/A Middle — N/A Tip — N/A. Spine shape: N/A. Spine length: N/A. Spine width: N/A. Spine apex descriptor: N/A. Spine color: N/A.

*Bud shape*.—Elliptic. Length: 0.5 cm. Diameter (base): 0.12 cm. Diameter (tip): 0.1 cm. Color: RHS 144A. Texture: Mildly pubescent.

*Winter hardiness*.—Unknown for 'HFG B2008T' outside of USDA Hardiness Zone 9b (Watsonville, Santa Cruz County, California USA). This cultivar is best adapted to the mild coastal conditions of California.

*Drought/heat tolerance*.—Pollen viability and fruit quality of blackberry generally begins to decline above 30° C. This is consistent with observations of 'HFG B2008T'. Blackberries are generally drought tolerant, however 'HFG B2008T' has not been tested under unirrigated conditions.

Leaves (Average of Floricane and Primocane Data)

*Complete leaf*.—

*Shape of leaf in cross-section*.—Simple cordate leaflet. Length: 26.2 cm. Width: 18.1 cm. Number of leaflets: 3 to 5.

*Terminal leaflet*.—Size: Length: 8.7 cm. Width: 7.2 cm. Length/width ratio: 1.2. Shape of leaf: Palmate. Apex: Acute. Shape of leaf base: Terminal leaf: Cordate. Basal lateral leaflets: Cordate. Margin: Floricane: Doubly Serrate. Primocane: Triply Serrate. Texture: Mild interveinal blistering. Number of serrations/leaf: 98. Shape of serrations: Retroflexed-Flexuous. Color: Floricane upper surface: RHS N137B. Floricane lower surface: RHS 147C. Primocane upper surface: RHS 137A. Primocane lower surface: RHS 146B. Venation pattern: Palmate. Venation Color: Floricane upper surface: RHS N137B. Floricane lower surface: RHS 146B. Primocane upper surface: RHS 137A. Primocane lower surface: RHS 144C. Leaf pubescence density: Moderate. Color of leaf pubescence: Floricane: RHS 146B. Primocane: RHS 144C. Number of leaflets/leaf: Primocane: 3 to 5. Floricane: 3. Interveinal blistering: Present, mild. Glossiness: High, Present. Time of leaf bud burst: Medium.

*Primocane leaves*.—Petiole length: 9.8 cm. Petiole diameter: 0.35 cm. Petiole color: Upper: RHS 144A. Lower: RHS 144A. Rachis length: 6.1 cm. Stipule length: 1.2 cm. Stipules per leaf: 2. Stipule width: 0.08 cm. Stipule color: RHS 144C. Color: Upper surface: RHS 137A. Lower surface: RHS 146B.

*Terminal leaflet*.—Length: 10.5 cm. Width: 8.7 cm. Rachis length: 4.5 cm.

*Distal lateral leaflet*.—Length: 9.9 cm. Width: 8.4 cm. Petiolule length: 2.8 cm.

*Basal lateral leaflet*.—Length: 9.9 cm. Width: 7.2 cm. Petiolule length: 0.6 cm.

*Floricane leaves*.—Petiole length: 5.1 cm. Stipule length: 1.1 cm. Stipules per leaf: 2. Stipule width: 0.2 cm. Stipule color: RHS 187A. Color: RHS 144A. Upper surface: RHS N137B. Lower surface: RHS 146B.

*Terminal leaflet*.—Length: 6.9 cm. Width: 5.7 cm.

*Distal lateral leaflet*.—Length: N/A. Width: N/A.

*Basal lateral leaflet*.—Length: 7.7 cm. Width: 7.0 cm.

*Petiolule*.—Length: 0.03 cm. Diameter: 0.02 cm. Color: Upper surface: RHS 146D. Lower surface: RHS 146D.

Flowers:

*Time of flowering* (50% *of plants at first flower*).—July 10 for Primocanes, April 25 for Floricanes.

*Size*.—Length: 1.5 cm. Diameter: 5.2 cm.

*Fragrance*.—Light floral rose scent.

*Peduncle*.—Length: 10.3 cm. Diameter: 0.26 cm. Color: RHS 143B. Pubescence: Puberulent. Texture: Soft from puberulence.

*Perianth*.—Flowering trusses shape: Truncate.

*Petals*.—Upper: RHS NN155B, margin is RHS 62D. Lower: RHS NN155B, margin is RHS 62D. Number per flower: 5. Shape: Obovate. Length: 2.4 cm. Width: 1.8 cm. Apex descriptor: Rounded. Base descriptor: Decurrent. Margin descriptor: Entire. Texture: Smooth with visible striations.

*Sepals*.—Quantity: 5. Length: 1.8 cm. Width: Base: 0.7 cm | Mid: 0.5 cm | Tip: 0.1 cm. Color: Upper surface: RHS 146B. Lower surface: RHS 146C. Apex descriptor: Acuminate. Margin descriptor: Entire. Texture: Puberulent.

*Pedicel*.—Color: RHS 143B. Length: 1.68 cm. Diameter: 0.15 cm.

Reproductive organs:

*Self-fertile*.—Yes.

*Male*.—Stamen number: 142. Filament length: 0.8 cm. Diameter: 0.01 cm. Color: RHS 157C. Anther length: 0.17 cm. Diameter: 0.1 cm. Color: RHS 145C. Pollen color: RHS 152C. Amount: Moderate.

*Female*.—Style length: 0.4 cm. Diameter: 0.01 cm. Color: RHS 145A. Stigma length: 0.01 cm. Diameter: 0.01 cm. Color: RHS 153A. Ovary length: 0.023 cm. Diameter: 0.005 cm. Color: RHS 145C.

Fruit:

*Fruiting length*.—Long.

*Predominant shape*.—Medium Ovate.

*Weight*.—10.4 g.

*Length*.—3.3 cm.

*Width*.—2.3 cm.

*Length/width ratio*.—1.43.

*Receptacle length*.—2.0 cm. Diameter: Base: 0.6 cm | Middle: 0.6 cm | Tip: 0.1 cm. Color: RHS 157A.

*Drupelet length*.—0.34 cm. Diameter: 0.26 cm. Number: 90. Drupelet weight: 0.1 g.

*Fruit color*.—External: RHS 203A. Internal: RHS 203A. Firmness of fruit skin.—Very firm. Firmness of fruit flesh: Very firm. Hollow center: Absent (torus present in blackberries). Number of fruits per node: 12-15 per fruiting lateral. Time of ripening (50% of plants with first fruit): 13-Jun on floricanes; 20-August on primocanes. Time of fruiting: Medium-late. Type of bearing: Remontant.

*Fruit yield*.—Floricanes: 11,000 lb/a. Primocanes: 14,000 lb/a. Average brix: 11.1. Market use: Fresh. Keeping quality: Excellent. Shipping quality: Excellent.

Pest and disease resistance: Field and substrate trials of 'HFG B2008T' have shown tolerance to *Agrobacterium tumefaciens*,downy mildew (*Peronospora sparsa*) and Botrytis. 'HFG B2008T' is susceptible to powdery mildew (*Sphaerotheca macularis*).

What is claimed is:

1. A new and distinct cultivar of Blackberry plant named 'HFG B2008T' as described and shown herein.

* * * * *